United States Patent [19]
Blatt et al.

[11] Patent Number: 5,945,345
[45] Date of Patent: *Aug. 31, 1999

[54] DEVICE FOR PREVENTING ASSAY INTERFERENCE USING SILVER OR LEAD TO REMOVE THE INTERFERANT

[75] Inventors: Joel M. Blatt, Palo Alto; Wilma M. Mangan, Santa Clara; Paul J. Patel; Victor A. Manneh, both of Sunnyvale, all of Calif.

[73] Assignee: Metrika, Inc., Sunnyvale, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/703,479

[22] Filed: Aug. 27, 1996

[51] Int. Cl.[6] ............................................. G01N 33/543
[52] U.S. Cl. ..................... 436/518; 436/514; 436/528; 436/530; 422/56; 422/57; 422/58; 422/60
[58] Field of Search ................... 422/56, 57, 58, 422/59, 60, 61, 63, 68.1, 81, 99, 100; 435/805, 962, 970; 436/175, 514, 535, 538, 518, 528, 529, 530, 824, 825, 525

[56] References Cited

U.S. PATENT DOCUMENTS

| | | | |
|---|---|---|---|
| 4,038,485 | 7/1977 | Johnston et al. | 23/230 B |
| 4,046,514 | 9/1977 | Johnston et al. | 23/253 TP |
| 4,053,281 | 10/1977 | Carter | 23/230 PC |
| 4,094,647 | 6/1978 | Deutsch et al. | 23/253 TP |
| 4,133,639 | 1/1979 | Harte | 23/230 B |
| 4,160,008 | 7/1979 | Fenocketti et al. | 422/56 |

(List continued on next page.)

FOREIGN PATENT DOCUMENTS

| | | | |
|---|---|---|---|
| 8000173 | 1/1980 | Netherlands | G01N 33/54 |
| 8808534 | 11/1988 | WIPO . | |
| 9201498 | 2/1992 | WIPO | G01N 33/92 |
| 9303175 | 2/1993 | WIPO . | |

OTHER PUBLICATIONS

Levinson, S. A. et al, Biochemistry, vol. 9(2), Jan. 20, 1970, pp. 322–331.

Prefilled Poly–Prep Columns for Ion Exchange Chromatography Instruction Manual, 7 pages, Bio–Rad Laboratories, Hercules, CA.

Millitrap, pp. 8–10, Waters Technical Service, Mitford, MA.

Nova–Clean IC, Bulletin #264, 7 pages, Alltech Associates, Deerfield, IL.

Installation Instructions and Troubleshooting Guide for Onguard Cartridges, 20 pages, Dionex, Sunnvale, CA.

Bond Elut and Mega Bond Elut, pp. 1–29, Varian Sample Preparation Catalog, Varian Associates, Palo Alto, CA.

Joyce, et al., Trace Level Determination of Bromate in Ozonated Drinking Water Using Ion Chromatography, J. Chromatogr. A, 671 (1994) pp. 165–171.

A Dot–Immunobinding Assay for Monoclonal and Other Antibodies, Richard Hawkes, Evelyn Niday, and Julian Gordon, Analytical Biochemistry 119, pp. 142–147 (1982).

(List continued on next page.)

*Primary Examiner*—James C. Housel
*Assistant Examiner*—Ginny Allen Portner
*Attorney, Agent, or Firm*—Timothy H. Gens; Trial & Technology Law Group

[57] ABSTRACT

The present invention provides a filter for effectively removing substances from a sample of bodily fluid which can interfere with the results of an assay. The filter includes a solid phase support and an active chemical component for binding to the interfering substance. The active chemical component is insoluble in the sample and is immobilized on the solid phase support. The present invention also includes a filter device, transport matrix, assay device, and method for removing substances which interfere with determining the presence of one or more analytes in a sample.

15 Claims, 8 Drawing Sheets

U.S. PATENT DOCUMENTS

| | | | |
|---|---|---|---|
| 4,168,146 | 9/1979 | Grubb et al. | 23/230 B |
| 4,233,402 | 11/1980 | Maggio et al. | 437/7 |
| 4,235,601 | 11/1980 | Deutsch et al. | 23/230 R |
| 4,275,149 | 6/1981 | Litman et al. | 435/7 |
| 4,281,061 | 7/1981 | Zuk et al. | 435/188 |
| 4,288,228 | 9/1981 | Oberhardt | 13/230 R |
| 4,288,541 | 9/1981 | Magers et al. | 435/14 |
| 4,313,734 | 2/1982 | Leuvering | 23/230 B |
| 4,361,537 | 11/1982 | Deutsch et al. | 422/56 |
| 4,366,241 | 12/1982 | Tom et al. | 435/7 |
| 4,373,932 | 2/1983 | Gribnau | 436/501 |
| 4,376,110 | 3/1983 | David et al. | 436/513 |
| 4,435,504 | 3/1984 | Zuk et al. | 435/7 |
| 4,446,232 | 5/1984 | Liotta | 435/7 |
| 4,517,288 | 5/1985 | Giegel et al. | 435/7 |
| 4,552,839 | 11/1985 | Gould et al. | 435/7 |
| 4,627,445 | 12/1986 | Garcia et al. | 128/770 |
| 4,637,403 | 1/1987 | Garcia et al. | 128/770 |
| 4,703,017 | 10/1987 | Campbell et al. | 436/501 |
| 4,756,884 | 7/1988 | Hillman et al. | 422/73 |
| 4,774,192 | 9/1988 | Terminiello | 436/530 |
| 4,787,398 | 11/1988 | Garcia et al. | 128/770 |
| 4,790,979 | 12/1988 | Terminello | 422/56 |
| 4,843,020 | 6/1989 | Woodford | 436/518 |
| 4,855,240 | 8/1989 | Rosenstein et al. | 436/514 |
| 4,861,711 | 8/1989 | Friesen et al. | 436/7 |
| 4,868,108 | 9/1989 | Bahar | 435/7 |
| 4,943,522 | 7/1990 | Eisinger | 435/7 |
| 4,956,302 | 9/1990 | Gordon et al. | 436/161 |
| 5,006,474 | 4/1991 | Horstman et al. | 436/524 |
| 5,036,000 | 7/1991 | Palmer et al. | 435/26 |
| 5,114,350 | 5/1992 | Hewett | 435/288 |
| 5,155,025 | 10/1992 | Allen et al. | 435/11 |
| 5,179,005 | 1/1993 | Phillips et al. | 435/14 |
| 5,212,060 | 5/1993 | Maddox | 435/7.1 |
| 5,213,965 | 5/1993 | Jones | 435/11 |
| 5,223,219 | 6/1993 | Subramanian | 422/55 |
| 5,250,439 | 10/1993 | Musho et al. | 435/25 |
| 5,354,692 | 10/1994 | Yang et al. | 436/514 |
| 5,401,466 | 3/1995 | Foltz et al. | 422/56 |
| 5,409,664 | 4/1995 | Allen | 422/56 |
| 5,415,994 | 5/1995 | Imrich | 435/5 |
| 5,416,000 | 5/1995 | Allen et al. | 435/7.92 |
| 5,426,030 | 6/1995 | Rittersdorf et al. | 435/11 |
| 5,459,080 | 10/1995 | Adamczyk et al. | 436/538 |
| 5,501,949 | 3/1996 | Marshall | 435/5 |
| 5,527,712 | 6/1996 | Sheehy | 436/525 |
| 5,541,069 | 7/1996 | Mortensen et al. | 435/7.9 |
| 5,563,042 | 10/1996 | Phillips et al. | 435/14 |
| 5,569,608 | 10/1996 | Sommer | 436/518 |
| 5,571,725 | 11/1996 | Pohl et al. | 436/161 |
| 5,582,907 | 12/1996 | Pall | 424/287 |
| 5,605,662 | 2/1997 | Heller et al. | 422/68.1 |
| 5,607,863 | 3/1997 | Chandler | 436/518 |
| 5,753,519 | 5/1998 | Durst et al. | 436/518 |

OTHER PUBLICATIONS

Detection of Specific Hybridoma Clones by Replica Immunoadsorption of Their Secreted Antibodies, Jacqueline Sharon, Sherie L. Morrison, and Elvin A. Kabat, Dec. 7, 1978, Proc. Natl. Acad. Sci. USA vol. 76, No. 3, pp. 1420–1424 Mar. 1979.

Home Cholesterol Testing, Editorial, The Lancet, vol. 340, Dec. 5, 1992 No. 8832, p. 1386.

Reliability and Feasibility of Pregnancy Home–Use Tests: Laboratory Validation and Diagnostic Evaluation by 638 Volunteers, Joelle Daviaud, Dominique Fournet, Chantal Ballongue, Guy–Pierre Guillem, Alain LeBlanc, Claude Casellas, and Bernard Pau, Clin. Chem. 39/1, 53–59 (1993).

A Multilayaer Membrane System for Blood Plasma Isolation for Use in Primary Health Care, APM Van Oudheusden and HDW Roesink, Ann Clin Biochem 1991; 28: 55–59.

Instrument–Free Quantitative Test Systems, Michael P. Allen and Prithipal Singh, Applications of Diagnostics, pp. 147–176 (1990).

DEVICE FOR PREVENTING ASSAY INTERFERENCE USING SILVER OR LEAD TO REMOVE THE INTERFERANT

RELATED APPLICATIONS

The subject matter of this application is related to a disposable single-use digital electronic instrument that is entirely self-contained, including all chemistry reagents, as disclosed in U.S. application Ser. No. 08/455,236 entitled "Novel Disposable Electronic Assay Device" filed May 31, 1995 by Michael P. Allen, U.S. application Ser. No. 08/657,894 entitled "Electronic Assay Device And Method" filed Jun. 7, 1996 by Michael P. Allen et al., U.S. application Ser. No. 08/512,844 entitled "Dry Reagent Particle Assay And Device Having Multiple Test Zones And Method Therefor" filed Aug. 9, 1995 by Joel M. Blatt and Michael P. Allen, and U.S. application Ser. No. 08/564,441 entitled "Method And Device For Blood Separation In A Diagnostic Device" filed Nov. 29, 1995 by Joel M. Blatt et al. The above applications have the same assignee as the present invention and are incorporated herein by reference in their entirety.

FIELD OF THE INVENTION

The present invention relates to a method and device for separating from assay samples one or more substances which may interfere with the assay results with sufficient speed and efficiency for immediate use in a diagnostic device.

BACKGROUND OF THE INVENTION

Many qualitative and quantitative diagnostic self-tests have developed in the clinical field utilizing bodily fluids from humans or animals as a sample. Although some of these techniques can be carried out directly using the bodily sample, it is necessary with many diagnostic assays to remove impurities, biopolymers, cells, ions, or other interfering substances from the sample of bodily fluid to obtain an accurate analysis. For example, the interfering substances in the sample could adversely affect a measurement of either reflected or transmitted light of a diagnostic test relying on either of these measurement techniques. The results of both quantitative and qualitative assays can be deleteriously affected.

One common conventional technique for separating interfering substances from a bodily fluid sample is by centrifugation. This technique, however, is time consuming and requires equipment that is not generally available outside of the clinical laboratory. For these reasons, centrifugation is entirely inappropriate for performing diagnostic self-tests by consumers or by professionals in point-of-care facilities.

In the example where red blood cells are the substance which interferes with the analysis of a blood sample, a common technique of separating red blood cells from plasma is to use a filtering device. Numerous materials have been used to form filters. Paper, fabric, glass or synthetic fibers, and membrane materials having a suitable pore size appear in the prior art.

For example, U.S. Pat. No. 4,816,224 to Vogel discloses a device for separating plasma or serum from whole blood and analyzing the serum using a glass fiber layer having specific dimensions and absorption to separate out the plasma from the whole blood for subsequent reaction. Among the problems of using glass fibers alone or in an admixture with other fibers is the slow rate of penetration by whole blood and the tendency to clog easily with practical yields of plasma usually being less than 25%. Furthermore, only small amounts of plasma or serum are entirely devoid of red blood cells or hemoglobin contamination which could interfere with subsequent quantitative measurements.

Another example is U.S. Pat. No. 4,753,776 to Hillman et al. which disclose a method of separating plasma from blood using a capillary force to drive the blood through fibers to a reaction area. Once the reaction area is saturated, the capillary force ceases and the transportation of the blood through the fibers and onto the reaction area stops. Two specific filtering media are disclosed: glass fibers alone or other cellulose materials fibers using a soluble red cell agglutinin added in free form to the filtration medium. The free form of agglutinin, however, can migrate from the fibers to contaminate the plasma with the red blood cells bound to the agglutinin. Also, a portion of the plasma is unusable because it remains in the filter to fill the void volume created in the bed of fibers.

For other interfering substances, Whatman Inc. of Fairfield, N.J. manufactures Specialized Chromatography Papers, such as model P-81, which are derivatized papers or derivatized cellulose loaded papers for use in the biotechnology processing industry for protein purification as well as in the analytical laboratory. These derivatized cellulose loaded papers use the known diagnostic capabilities of cellulose and glass fiber matrices with affinity binding chemistries for the removal of DNA binding proteins.

These prior art methods have proven unsuitable for applications involving diagnostic devices with space and volume restraints. Diagnostic devices also require an efficient method of removing interfering substances from a minute sample of bodily fluid, often just one drop, to produce a sufficient volume of usable sample to be transported through the assay portion of the device. The time allowed to complete the separation of the sample is also important so that the reaction chemistry can be accurately completed and the results are provided in a timely manner for the convenience of the user.

Thus, a need exists in the field of diagnostics for a means of removing interfering substances from assay samples which is sufficiently timely, efficient, and reliable for use in a diagnostic device which permits point-of-care use by untrained individuals in locations such as the home, sites of medical emergencies, or locations other than a clinic.

SUMMARY OF THE INVENTION

The present invention provides a filter for removing one or more substances from a sample which may interfere with determining the presence of an analyte in an assay sample. The filter includes a solid phase support and an active chemical component having an affinity for binding to and immobilizing the interfering substance. The active chemical component is insoluble in the sample and is immobilized on the solid phase support.

Another filter provided by the present invention includes a housing defining an interior space. The housing has an inlet and an outlet to provide fluid communication between the interior space and the exterior of the housing. A solid phase support is immobilized within the interior space. The filter includes means for physically retaining the solid phase support within the housing and an active chemical component having an affinity for binding to and immobilizing the interfering substance. The active chemical component is immobilized on the solid phase support and is insoluble in the sample.

The present invention also provides a filter device for releasably retaining a sample of bodily fluid and removing one or more assay interfering substances prior to delivery of the sample for assay. The device includes a body having at least one surface defining an interior cavity for releasably retaining the sample. An active chemical component as described above is immobilized within the body.

One embodiment of the present invention is a transport matrix for removing one or more substances which interfere with determining the presence of an analyte in an assay sample. The transport matrix includes a sample receptor zone configured to receive the sample and a detection zone having a reagent yielding a physically detectable change which correlates with the amount of selected analyte in the sample. The detection zone is in fluid communication with the sample receptor zone. An active chemical component, as described above, is immobilized on the transport matrix prior to the detection zone.

Another embodiment of the present invention is an assay device for removing one or more substances which interfere with determining the presence of an analyte in an assay sample. The assay device includes a housing having an exterior surface and a sample receptor means for receiving the sample containing an analyte selected for determining its presence. The sample receptor means is located on the exterior surface of the housing. The assay device includes a transport matrix as described above.

The present invention also provides a method of removing one or more substances which interfere with determining the presence of an analyte in an assay sample. The method includes the steps of: introducing the sample to a solid phase support; immobilizing the interfering substance on the solid phase support to form a clean sample; transporting the clean sample to a reaction zone; and chemically reacting the clean sample with at least one reagent to yield a physically detectable change which correlates with the amount of the corresponding selected analyte in the clean sample.

It is a further object of the present invention to provide a filter which occupies a volume sufficiently small and of a configuration adaptable for use with an assay strip within a diagnostic device.

Another object of the present invention is to provide a filter and method for removing interfering substances from a sample of bodily fluid so that the reaction chemistry of a diagnostic device can be accurately completed and the results are provided in a timely manner for the convenience of the user.

Other and further advantages, embodiments, variations and the like will be apparent to those skilled-in-the-art from the present specification taken with the accompanying drawings and appended claims.

BRIEF DESCRIPTION OF THE DRAWINGS

In the drawings, which comprise a portion of this disclosure.

DESCRIPTION OF THE PREFERRED EMBODIMENTS

Figure 1:
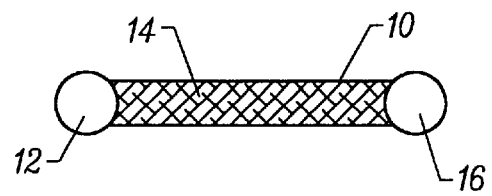
FIG. 1 is a top surface view of a diagnostic test device that can be used for quantitative and qualitative assays of samples in accordance with the present invention.

The present invention is preferably utilized in the disposable single-use digital electronic instrument and assay devices described in detail in the above-identified patent applications previously incorporated by reference. The present invention is also usable with qualitative and non-instrumented diagnostic devices. A sample of bodily fluid is applied directly to any type of diagnostic device which relies upon the removal of one or more substances from the sample which may interfere with an accurate analysis of the sample.

Generally, the present invention non-diffusively immobilizes an active chemical component upon a solid phase support to provide a zone in the path through which the sample of bodily fluid flows. The active chemical component is insoluble within the sample and exhibits an affinity for binding to the interfering substance. As a result, the interfering substance is indirectly immobilized upon the solid phase support and removed from the sample to yield a clean sample. The removal of the interfering substance from the sample is more efficiently and timely completed than compared to the prior art and suitable for use in a wide variety of diagnostic devices either as a free-standing filter or integrally formed with the device.

The solid phase support can be any solid material to which an active chemical component can be immobilized and include, but are not intended to be limited to, beads, magnetic particles, paramagnetic particles, microparticles or macroparticles, test tubes, swabs, droppers or other devices which are used to obtain a sample of a bodily fluid, capillaries, sponges, fabric or mesh that is woven or cast, and microtiter plates or other glass surfaces. Such solid phase support can be made from synthetic materials, naturally occurring materials, or naturally occurring materials which have been synthetically modified, and include, but are not intended to be limited to, cellulose materials, such as paper, cellulose and cellulose derivatives such as cellulose acetate and nitrocellulose; fiberglass; naturally occurring cloth such as cotton; synthetic cloth such as nylon; porous gels, such as silica, agarose dextrin, and gelatin; porous fibrous matrixes; starch based materials, such as cross-linked dextrin chains; ceramic materials; olefin or thermoplastic materials including polyvinyl chloride, polyethylene, polyvinyl acetate, polyamide, polycarbonate, polystyrene, copolymers of vinyl acetate and vinyl chloride, combinations of polyvinyl chloride-silica; and the like.

The term active chemical component as used herein includes any chemical or biochemical agent having an affinity for one or more of the interfering substances and capable of binding to the interfering substance and immobilizing the interfering substance on the solid phase support. The active chemical component must be insoluble within the assay sample so that it continues to be immobilized on the solid phase support. Affinity is the tendency of an atom, compound, or functional group to react or combine with some portion of the interfering substance having a different chemical constitution. The free energy decrease is a quantitative measure of chemical affinity. Active chemical components include, but are not limited to, antibodies to red blood cells and lectins. Immobilization can be conducted by covalent, ionic, hydrophobic, cross-linking, dipole-dipole, or other type of chemical binding to attach the active chemical component to the solid phase support. Immobilization can also be conducted by physical adsorption, as in activated carbon, molecular sieves, or other types of physical absorption.

Preferred active chemical components include derivatives of other solid phase supports:

Carboxymethyl (CM) polymer, e.g. cellulose, which is a weak cation exchanger with ether-linked methyl carboxylic acid Na+ function groups for binding of biopolymers, proteins, hormones and polypeptides bearing a positive charge within the range pH 4.5–10.5;

Diethylaminoethyl (DEAE) polymer, e.g. cellulose, which is a tertiary base anion exchanger is widely used in the commercial purification of monoclonal antibodies and recombinant DNA products and is a weak anion exchanger of moderate binding strength;

Sulfoxyethyl (SE) polymer, e.g. cellulose, is a strong acid cation exchanger has fully ionized Sulfoxyethyl groups particularly for cation exchange applications across a wide pH range;

Trimethylhydroxy propyl quaternary ammonium (QA) polymer, e.g. cellulose, is a strong base quaternary ammonium exchanger with fast kinetics, high protein capacity, and effective over a wide pH range;

Orthophosphate (P) polymers, e.g. cellulose, is a bifunctional strong and weak acid cation exchanger which shows a high affinity for multivalent cations including enzymes such as protein kinases, restriction enzymes, deaminases, nucleases, polymerases and inorganic ions such as calcium and iron; and IminoDicarboxylic Acid (IDA) is a material having a crossed-linked regenerated celluloid.

Other preferred active chemical components include derivatives of the following solid phase supports: diethylaminoethyl Sephadex, diethyl[2-hydroxypropl] aminoethyl Sephadex, Sepharose, epichlorohydrin triethanolamine cellulose, polyethyleneimine cellulose, quaternary alkylamine, quaternary alkylalkanolamine, trimethylbenzylammonium, dimethylethanolbenzylammonium, trimethylbenzylammonium, dimethylethanolamine, polyamine, alkylamine, quaternary ammonium, tertiary amine, carboxymethyl Sephadex, sulfopropyl Sephadex, sulfoxyethyl cellulose, sulfonic acid, nuclear sulfonic acid, carboxylic acid, and triethylaminoethyl cellulose.

The term derivatized cellulose as used herein includes the products from reacting cellulose such as wood pulp or cotton with acetic acid or acetic anhydride and a sulfuric acid catalyst. The cellulose is fully acetylated with three acetate groups per glucose unit and at the same time the sulfuric acid causes appreciable degradation of the cellulose polymer so that the product contains only 200–300 glucose units per polymer chain. Usually the cellulose acetate is partially hydrolyzed by the addition of water until an average of about 2–2.5 acetate groups per glucose unit remain. The product is thermoplastic and soluble in acetone.

Other preferred active chemical components include the transition elements and, in particular, silver and lead. Other elements or compounds that have an affinity to form complexes with the interfering substance are also suitable.

The amount of the active chemical component immobilized on the solid phase support is preferably in sufficient excess over the quantity of interfering substance estimated to be in a sample. The active chemical component can have one or more reactive sites which can bind to one or more sites on a corresponding interfering substance. It is desirable to provide an excess amount of the active chemical component to allow for some reactive sites which may fail to bind to an interfering substance.

A preferred derivative content for the weight of active chemical component on an area of solid phase support is less than 10 mg/cm$^2$ which effectively immobilizes the interfering substance. A preferred range for the derivative content of the active chemical component on the solid phase support is about 3.0 mg/cm$^2$ to about 1.0 mg/cm$^2$. The most preferred range for the derivative content of the active chemical component and the solid phase support is about 2.5 mg/cm$^2$ to about 2.0 mg/cm$^2$.

A preferred amount of the active chemical component applied on the solid phase support is in an amount less than about 1M which effectively immobilizes the interfering substance. Usually, about 0.05M is a minimum effective amount of the active chemical component. A more preferred amount of active chemical component present on the solid phase support is in the range of about 0.1M to about 0.8M.

The present invention can be used to remove many types of substances which potentially interfere with the results of an assay. In particular, the preferred embodiments of the present invention are effective in significantly reducing the interference from salts such as sodium chloride and other interfering substances like ascorbate, bilirubin, and uric acid.

Substantially all types of assays can be carried out with the present invention for a wide variety of analytes. Assays that can be performed include, but are not limited to, general chemistry assays and immunoassays. Both endpoint and reaction rate type assays can be accomplished with the present invention.

Analyte, as used herein, is the substance to be detected which may be present in the test sample. For example, general chemistry assays can be performed for analytes such as, but not limited to, glucose, cholesterol, HDL cholesterol, LDL cholesterol, triglycerides, and BUN. For immunoassays, the analyte can be any substance for which there exists a naturally occurring specific binding member (such as, an antibody), or for which a specific binding member can be prepared. Thus, an analyte is a substance that can bind to one or more specific binding members in an assay. Analyte also includes any antigenic substances, haptens, antibodies, macromolecules, and combinations thereof. As a member of a specific binding pair, the analyte can be detected by means of naturally occurring specific binding partners (pairs) such as the use of intrinsic factor protein as a member of a specific binding pair for the determination of Vitamin B12, or the use of lectin as a member of a specific binding pair for the determination of a carbohydrate. The analyte can include a protein, a peptide, an amino acid, a hormone, a steroid, a vitamin, a drug including those administered for therapeutic purposes as well as those administered for illicit purposes, a bacterium, a virus, and metabolites of or antibodies to any of the above substances. In particular, such analytes include, but are not intended to be limited to, ferritin; creatinine kinase MB (CK-MB); digoxin; phenytoin; phenobarbital; carbamazepine; vancomycin; gentamicin, theophylline; valproic acid; quinidine; luteinizing hormone (LH); follicle stimulating hormone (FSH); estradiol, progesterone; IgE antibodies; vitamin B2 micro-globulin; glycated hemoglobin (Gly Hb); cortisol; digitoxin; N-acetylprocainamide (NAPA); procainamide; antibodies to rubella, such as rubella-IgG and rubella-IgM; antibodies to toxoplasma, such as toxoplasmosis IgG (Toxo-IgG) and toxoplasmosis IgM (Toxo-IgM); testosterone; salicylates; acetaminophen; hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B antigen (HBAg); antibodies to hepatitis B antigen (Anti-HB); thyroid stimulating hormone (TSH); thyroxine (T4); total triiodothyronine (Total T3); free triiodothyronine (Free T3); carcinoembryonic antigen (CEA); and alpha fetal protein (AFP). Drugs of abuse and controlled substances include, but are not intended to be limited to, amphetamine; methamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; methaqualone; opiates such as heroin, morphine, codeine, hydromorphone, hydrocodone, methadone, oxycodone, oxymorphone, and opium; phencyclidine; and propoxyphene. The details for the preparation of such antibodies and their suitability for use as specific binding members are well known to those skilled in the art.

The sample to be tested by the present invention for the presence of an analyte can be derived from any biological source, such as a physiological fluid, including whole blood or whole blood components including red blood cells, white blood cells, platelets, serum and plasma; ascites; urine; sweat; milk; synovial fluid; peritoneal fluid; amniotic fluid; cerebrospinal fluid; and other constituents of the body which may contain the analyte of interest. The test sample can be pre-treated prior to use, such as preparing plasma from blood, diluting viscous fluids, or the like; methods of treatment can involve filtration, distillation, concentration, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte. The analyte can be any compound or composition to be detected or measured and which has at least one epitope or binding site.

Single or multiple assays can be done at one time. For example, a single assay can be performed measuring cholesterol or one device can be set up to measure both total and HDL cholesterol from a single sample. One test device can be set up to measure one, two, three, or more analytes at one time.

The present invention can be used in assay devices having many configurations, some of which are specifically illustrated herein. Often these assay devices use a wicking member or transport matrix which is a porous material. By "porous" is meant that the material is one through which the test sample can easily pass and includes both bibulous and non-bibulous solid phase materials. In the present invention, the porous member can include a fiberglass, cellulose, or nylon pad for use in a pour and flow-through assay device having multiple layers for multiple assay reagents; a test strip for wicking or thin layer chromatographic capillary action (e.g., nitrocellulose) techniques; or other porous or open pore materials well known to those skilled in the art (e.g., polyethylene sheet material).

The assay devices include a sample receptor means for receiving a sample of bodily fluid, such as whole blood, containing at least one of a plurality of analytes selected for determining its presence. The sample receptor means is located on the exterior surface of the device housing and allows the sample to be applied to a sample pad, wicking material, transport matrix or the like. Subsequently, the interfering substances are removed from the sample to form a "clean" sample.

The clean sample is in fluid communication with a sample treatment means for chemically reacting the clean sample with at least one chemical reagent corresponding to an assay. Each reagent chemically reacts with the clean sample in a corresponding reaction zone located on the transport matrix to produce a reaction product mixture corresponding to each reagent. The sample treatment means also transports at least a portion of each reaction product mixture to a corresponding detection zone located on the transport matrix. The sample treatment means is located within the housing and is in fluid communication with the sample receptor means. Alternately, the clean sample can react with the chemical reagent in the detection zone.

For immunoassays, the present invention preferably uses particle detection for a detectable response or signal in each reaction zone related to the level of analyte in the sample. Other means for providing a detectable response in the reaction zones are suitable for use in the present invention. For example, and not for limitation, the analyte may be labeled with an indicator to measure fluorescence or luminescence, or the reflectance or absorption of a characteristic light wavelength. As use herein, "indicator" is meant to include all compounds capable of labeling the analyte or conjugate thereof and generating a detectable response or signal indicative of the level of analyte in the sample.

Although the chemistry and configurations of the present invention may be used in an integrated assay device, the present invention can be used in any other instrumented reflectance or transmission meter as a replaceable reagent. Thus, the present invention also encompasses integrated assay instruments and analytical assay instruments comprising the present assay device.

A single channel test device 10 utilized in some of the experimental investigations described below is set forth in FIG. 1. The device 10 includes a sample pad 12 in fluid communication with a wick material 14. The wick material 14 transports the sample across its length. Similarly, an end pad 16 terminates the wick material 14 at the end opposite the sample pad 12. A sample potentially containing interfering substances is applied at the sample pad 12 and is separated into a clean sample while the interfering substances are retained on the sample pad 12. The clean sample passes through the wick material 14 and reaches the end pad 16.

Figure 2:
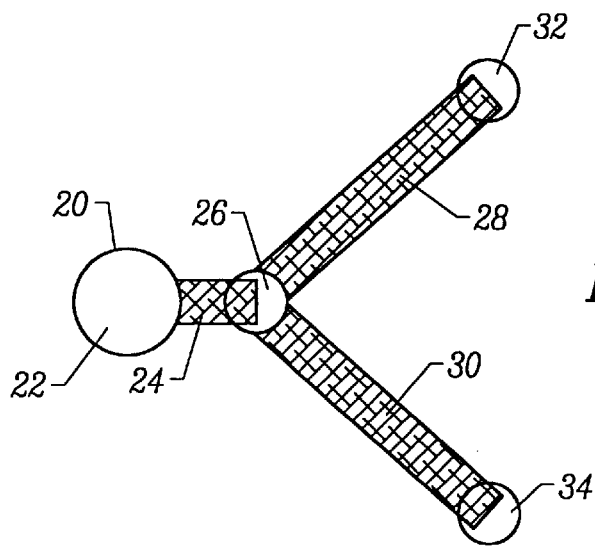
FIG. 2 is a top surface view of another diagnostic test device that can be used for simultaneous multiple quantitative and qualitative assays of samples in accordance with the present invention.

Referring now to FIG. 2, a dual channel test device 20 utilized in the investigations described below is illustrated. The device 20 includes a sample pad 22 in fluid communication with a bridge 24 which connects to a distribution pad 26. Two separate wick materials 28 and 30 are in fluid communication at one end with the distribution pad 26 and at the opposite end with two reaction pads 32 and 36, respectively. A sample potentially containing one or more interfering substances is applied at the sample pad 22 and is separated into a clean sample while any interfering substances are retained in the sample pad 22. The clean sample is transported by the bridge 24 and saturates the distribution pad 26. The clean sample then proceeds simultaneously along the wick strips 28 and 30. The reaction pads 32 and 34 receive the clean sample for reaction with chemical reagents deposited thereon to perform two diagnostic assays simultaneously.

Figure 3:
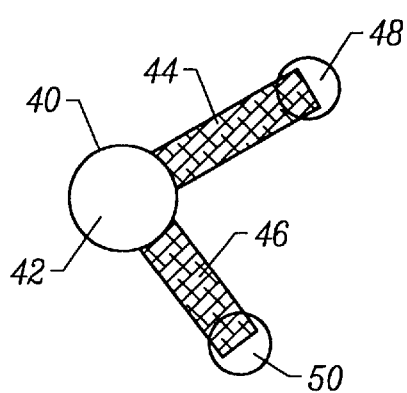
FIG. 3 is a top surface view of an embodiment of the present invention providing a diagnostic device for performing simultaneous multiple assays on samples.

One of the preferred embodiments of the present invention is a diagnostic device 40 illustrated in FIG. 3 for performing multiple assays simultaneously. The device 40 includes a sample pad 42 for receiving a sample potentially containing one or more interfering substances. The sample pad 42 includes a solid phase support which removes the interfering substances by binding them to an active chemical component immobilized on the solid phase support to yield a clean sample. Wicking strips 44 and 46 are in fluid connection with the sample pad 42 and transport the clean sample to respective reaction pads 48 and 50 which contain the chemical reagents necessary for performing the diagnostic assays.

Figure 4:
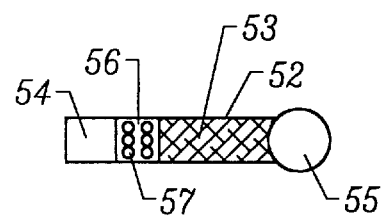
FIG. 4 is a top surface view of another embodiment of the present invention providing a diagnostic device for performing an assay on a sample.

Referring to FIG. 4, another preferred embodiment of the present invention is illustrated as a diagnostic device 52 for performing an assay. The device 52 includes a wicking strip 53 having a sample pad 54 at one end and a reaction pad 55 at the other end. After a sample potentially containing one or more interfering substances is applied to the sample pad 54, the sample flows through a zone 56 containing a plurality of microparticles 57 having an active chemical component immobilized thereon. The microparticles 57 provide a solid phase support which binds to the interfering substance. In turn, the microparticles 57 themselves are immobilized within the zone 56. The zone 56 provides a second solid phase which physically retains the microparticles 57 therein. The second solid phase can be the same or different material which comprises the sample pad 54 or the wicking strip 53.

Alternately, the active chemical component can be immobilized directly on the material which comprises the zone 56 rather than on the microparticles 57. In this embodiment, the material which comprises the zone 56 provides the solid phase support. The active chemical component is loaded onto the solid phase support. No second solid phase is used.

In another embodiment, the active chemical component is integral to the solid phase support. For example, the active chemical component can be a functional group of the solid phase support which has an affinity for one or more of the interfering substances.

Figure 5:
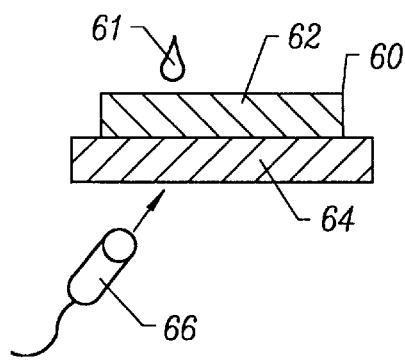
FIG. 5 is a cross-sectional side view of a sample pad and assay strip arranged in a stacked configuration for the separation of interfering substance from a sample in a diagnostic assay device.

FIG. 5 illustrates a stacked configuration for a diagnostic device 60 receiving a sample 61 potentially containing interfering substances. The device 60 includes a sample pad 62 which includes a solid phase support to remove any interfering substances by binding them to an active chemical component immobilized on the solid phase support. The resulting clean sample flows to a reaction pad 64 which contains the chemical reagents necessary to perform the diagnostic assay and yield a physically detectable change. In this configuration, a detector 66 is positioned to view the physically detectable change in the area of the reaction pad 64.

Figure 6:
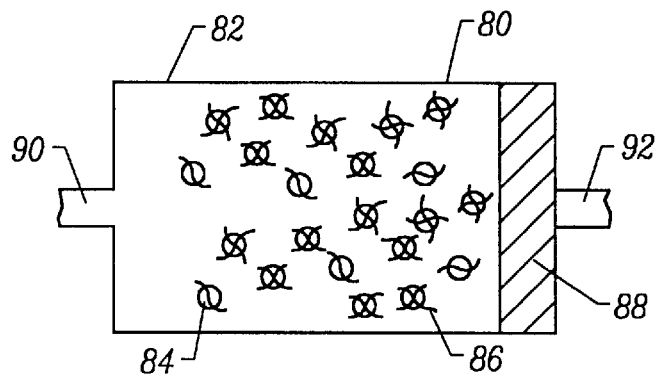
FIG. 6 is cross-sectional view of a container which houses a separation filter in accordance with the present invention.

The present invention also provides a filter 80 for separating interfering substances from a sample to form a clean sample which is subsequently analyzed as illustrated in FIG. 6. The filter 80 includes a container 82 which retains a solid phase support 84 in a zone within the flow path of the sample potentially containing one or more interfering substances. Immobilized on the solid phase support is an active chemical component 86 suitable for binding to any interfering substances in the sample. The solid phase support 84 and immobilized active chemical component is retained within the container 82 by a membrane 88 wholly permeable to the sample. The membrane 88 physically entraps the solid phase support 84 within the container 82. The sample potentially containing interfering substances enters the container through inlet 90 and the clean sample leaves through outlet 92.

Figure 7:
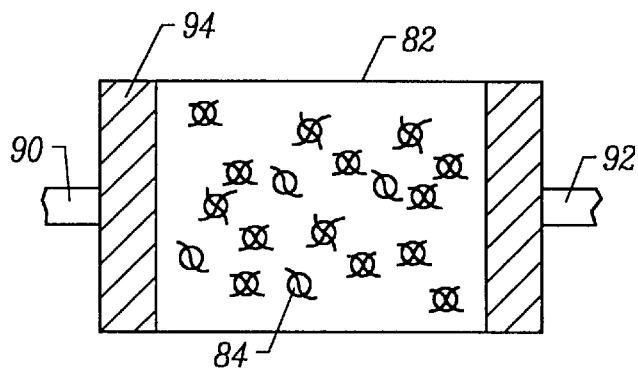
FIG. 7 is a cross-sectional view of an alternate embodiment of the separation filter in FIG. 6.

An alternate embodiment of the filter in FIG. 6 is illustrated in FIG. 7. The container 82 includes a second membrane 94 to retain the solid phase support 84 should the flow through the container be reversed. Reversing the flow through the container would be desirable, for example, to regenerate the binding capability of the active chemical component by removing the bound interfering substances. Any conventional method of cleaving the bond between the active chemical component interfering substances are suitable for use with the present invention. For example, the binding function of the active chemical component can be regenerated by treating the solid phase support 84 with a solution having a high ionic strength, a low pH value, or a denaturing agent. In another example, where a cell is the interfering substance, lysing the cell with a surfactant is another suitable regeneration treatment.

The embodiments of FIGS. 6 and 7 are particularly useful for automated testing equipment or high volume applications. The regeneration feature of the present invention with either embodiment provides a widespread applicability with low cost and convenience.

Figure 8:
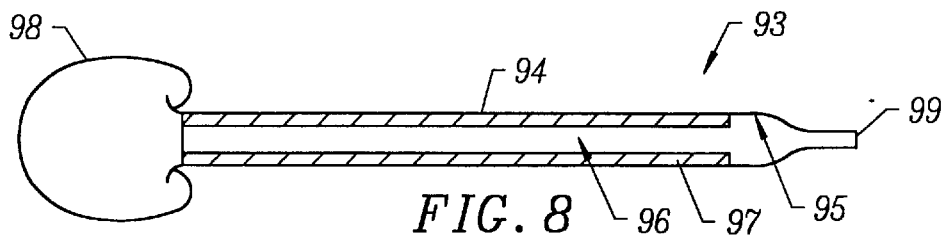
FIG. 8 is a cross-sectional view of another embodiment of a filter device which releasably retains a sample of bodily fluid and removes one or more assay interfering substances prior to delivery of the sample for assay.

Another embodiment of a filter device 93 is illustrated in FIG. 8 which releasably retains a sample of bodily fluid and removes one or more assay interfering substances prior to delivery of the sample for assay. The filter device 93 includes a body 94 having at least one surface 95 defining an interior cavity 96 for releasably retaining the sample. An active chemical component 97 having an affinity for binding to and immobilizing the interfering substance within the interior cavity 96 is immobilized directly on the surface 95. A compressible cap 98 attaches to one of the body 94 to draw the sample through an opening 99 in the body 94 and subsequently release the clean sample to the assay site.

An alternate embodiment of the filter device in FIG. 8 is to immobilize the active chemical component on a solid phase support as described above and in particular with regard to FIG. 7. In this alternate embodiment, the active chemical component and the solid phase support would be similarly retained with the interior cavity 96, whether the sample is being drawn into, or released from, the body 94.

The filter device 93 is preferably a type of applicator which can collect the bodily fluid, remove the interfering substance, and then deliver the clean sample to an assay site. Examples of the filter device include, but are not limited to, a dropper, pipette, vial, ampoule, syringe, sponge, and swab.

The embodiments described in reference to FIG. 8 are particularly useful for extracting or collecting samples of bodily fluids directly from human or animal subjects. Since the sample is immediately treated to remove the interfering substance, the clean sample can be directly applied to the site of a conventional assay device.

Figure 9:
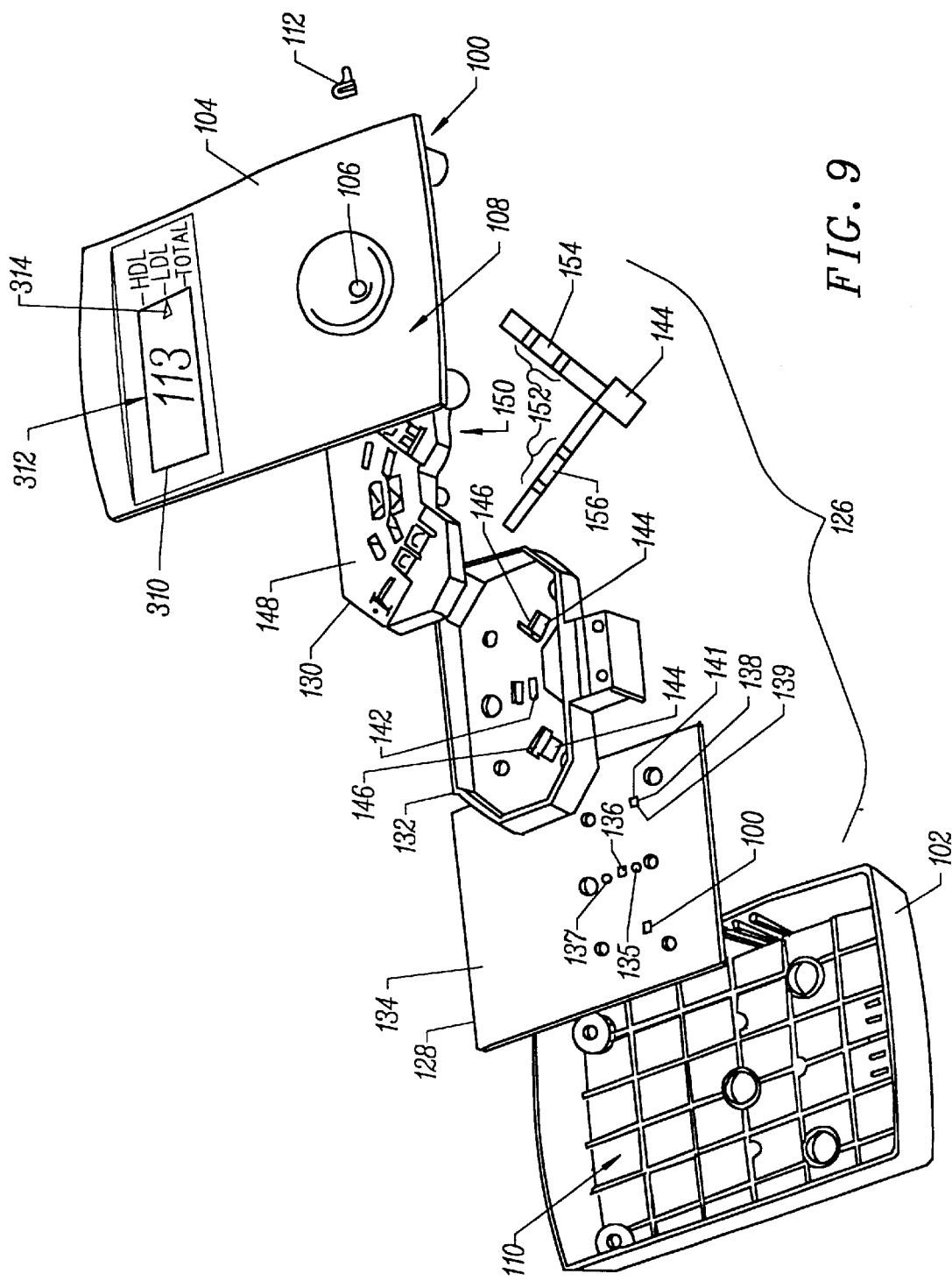
FIG. 9 is an exploded perspective view of a preferred embodiment of a diagnostic device of the present invention.

A preferred embodiment of a single-use diagnostic device 100 is illustrated in FIG. 9. The device 100 includes a housing 102 and cover 104 having a receptor such as inlet port 106 which extends from the exterior surface 108 of the cover to the interior 110 of the housing for receiving a sample 112 containing the one or more selected analytes to be determined.

The inlet port 106 allows the sample 112 to be introduced to a sample receiving device 114 which is attached to the interior surface 116 of the cover 104. The sample receiving device 114 includes a pad which is in fluid communication with two assay strips and serves to distribute the sample between the two strips. Optionally, the sample receiving device 114 can also include a sample filter pad which removes undesired contaminants from the sample. The sample filter pad can be the same as the receiving pad with one pad performing bother functions. The device 100 can include more than one sample filter pad along the pathway of the sample flow which remove different types of contaminants. The two assay strips contain chemical reagents for determining the presence of one or more selected analytes.

The interior 110 of the housing encloses a reflectometer 126 which includes a printed wiring assembly having a printed circuit board (PCB) 128. The reflectometer 126 also includes an optics assembly 130 and a shield 132. The PCB 128 has one face 134 with a reference detector 136 and zone detectors 138, 140 mounted directly thereto. The face 134 of the PCB also has two LEDs 135, 137, one for each pair of illumination channels, mounted directly to the PCB. The LEDs 135, 137 are preferably in bare die form without an integral lens, enclosure, or housing. As a result, the LEDs 135, 137 provide illumination in all directions above the face 134 and are directed only by the optics assembly 130. Similarly, the zone detectors 138, 140 and reference detector 136 are bare die mounted directly to the face 134 of the PCB. The LEDs 135, 137 and the detectors 136, 138, 140 are all positioned in the same plane.

FIG. 9 also illustrates the position of the shield 132 relative to the PCB 128. Aperture 142 is provided through the shield 132 to prevent obstructing the LEDs 135, 137 and the reference detector 136. Openings 144 are provided to prevent obstructing zone detectors 138, 140. The shield 132 includes upstanding walls 146 which prevent stray radiation from entering the zone detectors 138, 140. The upstanding walls 146 are positioned adjacent the reflecting and refracting elements of the optics assembly 130 when the reflectometer 126 is fully assembled.

The optics assembly 130 is a generally planar support having at least a top face 148 and a bottom face 150. The bottom face 150 is configured to receive illumination from the LEDs 135, 137 and the optics assembly 130 directs the illumination to one or more sampling areas 152 on a first 154 and second 156 assay strip. The top face 148 of the optics assembly is also configured to transmit the diffusely reflected optical radiation returning from the sampling areas 152 to one or more of the zone detectors 138, 140.

Having generally described the present invention, a further understanding can be obtained by reference to the following specific examples, which are provided herein for purposes of illustration only and are not intended to be limiting of the present invention.

EXAMPLE 1

An example of a substance which potentially interferes with accurate assay results of bodily fluids are salts such as sodium chloride. The chloride ions released from sodium chloride dissolved in the bodily fluid often decreases the color contrast in a general immunoassay.

To demonstrate the effectiveness of the present invention in solving this problem, samples containing measured amounts of sodium chloride were filtered to remove the chloride ions and provide a "clean" sample. In these tests, treated and untreated sample pads measuring 7×7 mm were prepared as illustrated by reference numeral 202 in FIGS. 10 and 11. The sample pad is one component for performing immunoassays using assay strip 200.

The sample pads were made from various types of materials to test their effectiveness at removing chloride from the sample. The different types of materials are summarized in Table 1. Each of the materials is designated with a suffix to indicate whether the material has been treated with an active chemical component. In this example, the various materials were treated with silver nitrate in order to bind silver in the material which is labeled with the -Ag suffix. If the material was not treated, the suffix -Na was used to indicate that each material as manufactured has some sodium bound to the material.

One of the sample pad materials used was SARTO-BIND™ IDA Lot #L64 from Sartorius of Edgewood, N.Y. which is an IminoDicarboxylic Acid (IDA) made into a material having a crossed-linked regenerated celluloid with a pore size of 3–5$\mu$ and a thickness of 250–300 $\mu$m. The IDA material has a protein binding capacity for metals of 30–50 mg/unit and a protein binding capacity for proteins of 100–200 mg/unit with a flow rate of 1 ml/min cm$^2$.

Another of the sample pad membrane materials was C/P30 from Whatman, Inc. of Fairfield, N.J. which is an orthophosphate cellulose (phosphocellulose) matrix having a basis weight of about 85 g/m$^2$, a thickness of about 259 $\mu$m, and a mean pore size of 17.0 $\mu$m. The C/P30 material has a protein binding capacity for Lysozyme of 0.1 g/dg with a linear wicking (Klemm) of 3 min for a 7.5 cm rise and a derivative content of 2.5 mg/cm$^2$. Phosphocellulose is a bifunctional strong and weak acid cation exchanger. It shows a high affinity for multivalent cations including enzymes such as protein kinases, restriction enzymes, deaminases, nucleases, polymerases and inorganic ions such as calcium and iron.

Another of the sample pad membrane materials was C/CM50 from Whatman, Inc. of Fairfield, N.J. which is an carboxymethyl cellulose matrix having a basis weight of about 85 g/m², a thickness of about 305 μm, and a mean pore size of 18.0 μm. The C/CM50 material has a protein binding capacity for Lysozyme of 0.57 g/dg with a linear wicking (Klemm) of 2.5 min for a 7.5 cm rise and a derivative content of 4.2 mg/cm². The C/CM50 material is a weak cation exchanger with ether-linked methyl carboxylic acid Na+ function groups that binds biopolymers, proteins, hormones and polypeptides bearing a positive charge within the range pH 4.5–10.5.

The procedure for the assays evaluating the ability of silver nitrate treated membranes to bind chloride included preparing solutions of NaCl with 6.25, 12.5, 25, 50, 75, 125, 250, and 750 mM with deionized water and pipetting 10 uL of each NaCl solution onto a separate sample pad. Each sample pad and NaCl solution was incubated for about 2 minutes and then placed into separate Eppendorff 1.5 cc microcentrifuge tubes. About 90 uL of deionized water was pipetted over sample pads to ensure that the pad was submerged in the water and then agitated to release the unbound chloride ions. All of the tubes were centrifuged at 12,000 RPM for 5 minutes.

Concurrently, 250 uL of a Sigma chloride reagent was pipetted into the wells of a flat-bottomed, 96 well microtiter tray. The Sigma Chloride reagent was catalog number 124H098. The tray was sealed and incubated at 37 degrees C. for 15 minutes to activate the chloride reagent.

About 5 uL of sample were pipetted into the wells of the microtiter tray containing the chloride reagent in order to provide a standard curve for the different (0, 6.25, 12.5, 25, 50, and 750 mM) NaCl solutions. About 5 uL of the supernatant from the centrifuged tubes was pipetted in triplicate into its respective well in the microtiter tray containing the chloride reagent.

The microtiter tray was incubated for about 5 minutes at 37 degrees C and allowed to set 10–15 minutes at room temperature before readings of each of the samples were taken on a microtiter plate reader MRX from Dynatech Laboratories at 450 nm. The results were expressed as a percentage reduction in chloride concentration remaining in the supernatant fluid.

Table 1 provides the results for three materials used to make the sample pad membranes with and without treatment with silver nitrate. As the test results demonstrate, the C/P30 and IDA materials bind a significant amount of chloride to effectively remove this substance from interfering with an assay. The CM50 material is suitable for binding much smaller quantities of chloride compared to the preferred C/P30 and IDA materials.

TABLE 1

| | Chloride Recovered (mM) | | | | | |
|---|---|---|---|---|---|---|
| Chloride Added(mM) | CM50-Na | CM50-Ag | IDA-Na | IDA-Ag | C/P30-Na | C/P30-Ag |
| 0 | 0 | 0 | 0 | 0 | 2.4 | 0 |
| 0.1 | 87.6 | 85.2 | 121.9 | 13.1 | 103 | 0 |
| 0.15 | 142.2 | 100.4 | 149.5 | 0 | 179 | 0 |
| 0.2 | 204.4 | 232.9 | 211.2 | 0 | 218 | 20 |
| 0.3 | 283.9 | 221.1 | 222 | 54.9 | 294 | 143.1 |

EXAMPLE 2

Silver nitrate treated sample pads were prepared by cutting strips of negatively charged membranes into 10×1.4 cm pieces. Two different membranes were tested: Sartorius IDA membrane Lot #L64 and Whatman C/P30 membrane Lot #87604.

Solutions of 0.6M AgNO₃ in deionized water were prepared fresh daily. About 4 cc of AgNO₃ was pipetted into a weigh boat. Each strip of the membranes was dipped into the AgNO₃ solution and then repeated while reversing the direction of dipping for a total of 2 dips. Each strip was blotted on filter paper from Schleicher & Schuell GB002 Lot #BG932.

Each membrane strip was then dipped in a bath (approximately 5–10 cc) of deionized water twice while turning the membrane strip between dipping. This water rinse procedure was repeated for a total of five washes. Each membrane strip was again blotted on filter paper.

The membrane strips were placed in an open foil ziplock bag and placed in an incubator at 37 degrees C. for about 20 minutes for the IDA membrane and about 40 minutes for the Whatman CP/30 membrane. Each of the membrane stripes was stored, protected from light, with desiccant packs in a dry room. The same procedure described in Example 1 was then followed. The results were expressed as a percentage reduction in chloride concentration remaining in the supernatant fluid.

Figure 12:
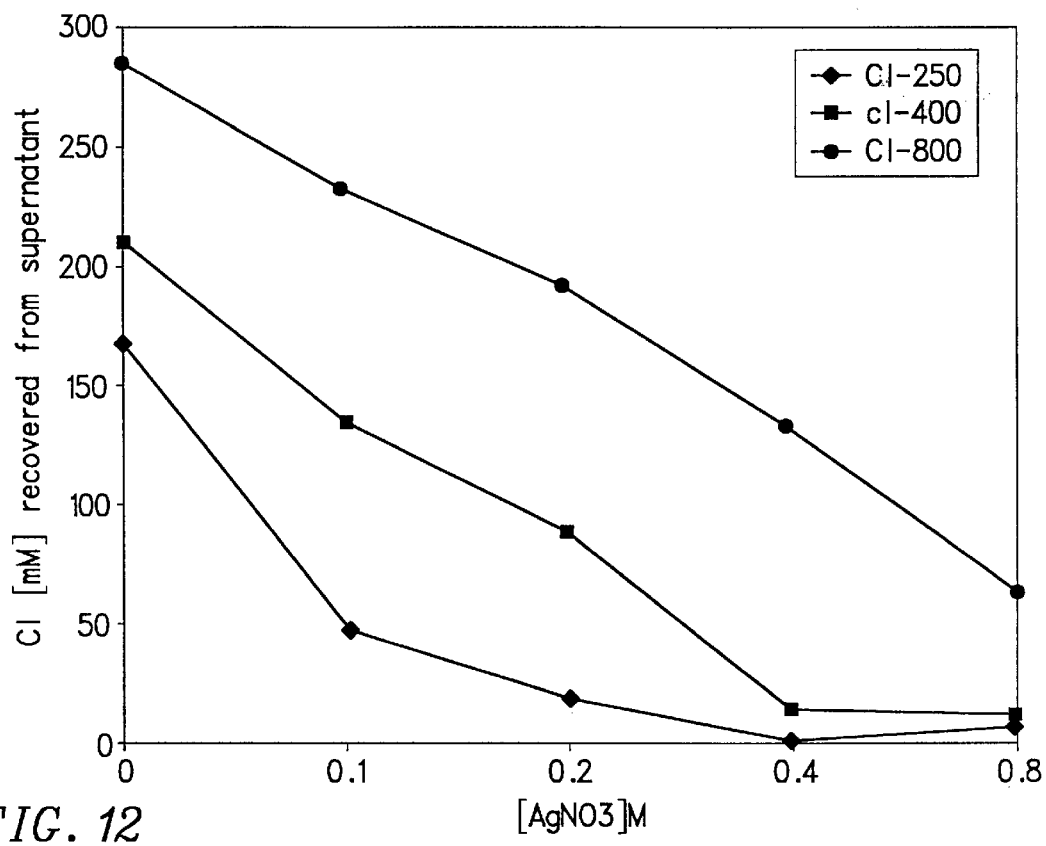
FIG. 12 is a graph of the chloride concentration (mM) recovered from supernatant vs. the silver nitrate concentration (M) for a silver treated C/P30 sample pad membrane at three initial concentrations (mM) of chloride (250, 400, and 800)

FIG. 12 illustrates the effect of silver nitrate treated sample pad membrane made of C/P30 for removing chloride from the sample. The results for three different chloride concentrations (250, 400, and 800) are provided across a range of silver nitrate from 0 to about 0.8M.

Figure 13:
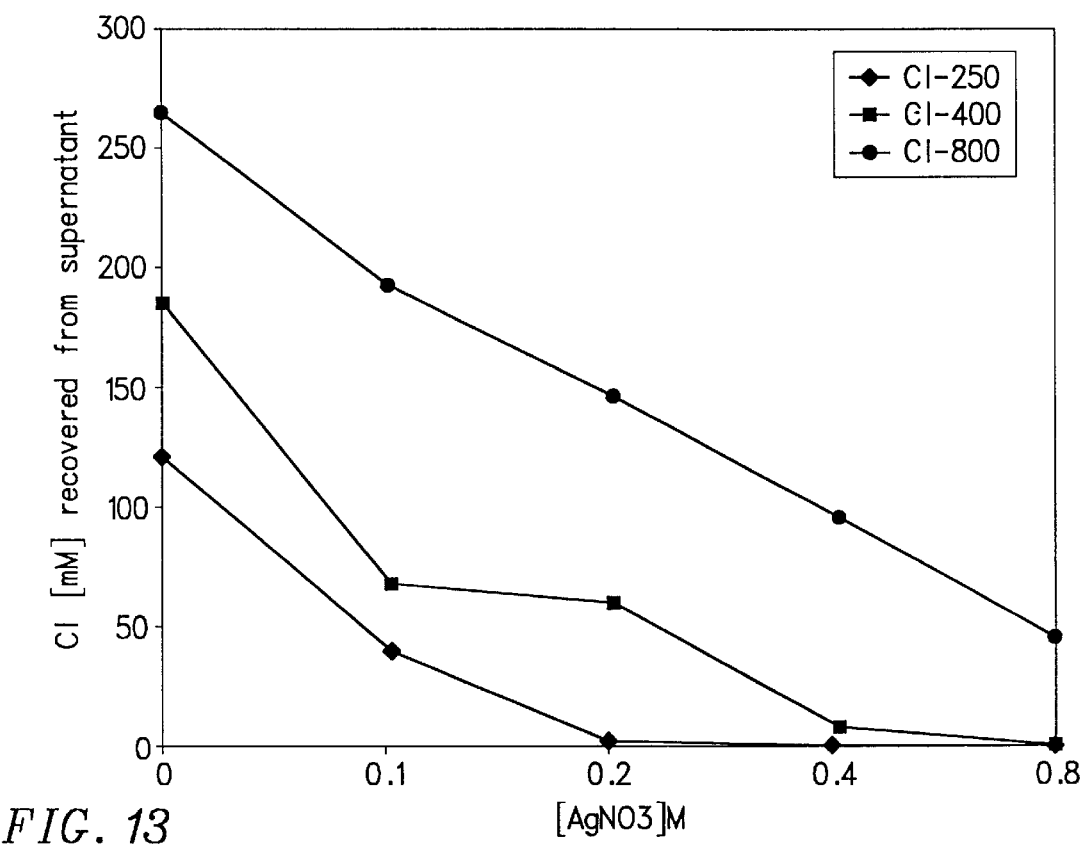
FIG. 13 is a graph of the chloride concentration (mM) recovered from supernatant vs. the silver nitrate concentration (M) for a silver nitrate treated IminoDicarboxylic Acid (IDA) sample pad membrane at three initial concentrations (mM) of chloride (250, 400, and 800)

FIG. 13 illustrates the effect of silver nitrate treated sample pad membrane made of IDA for removing chloride from the sample. The results for three different chloride concentrations (250, 400, and 800) are provided across a range of silver nitrate from 0 to about 0.8M.

EXAMPLE 3

Several test assays were performed to evaluate the ability of silver nitrate treated membranes to bind the assay interfering substance chloride. To demonstrate the effectiveness of the present invention in solving this problem, several tests were performed using an NTX™ (Ostex International) assay.

In these assays, treated and untreated sample pads measuring 7×7 mm were prepared as described in Example 2, except that the sample pads were only washed once after dipping instead of five times.

Figure 10:
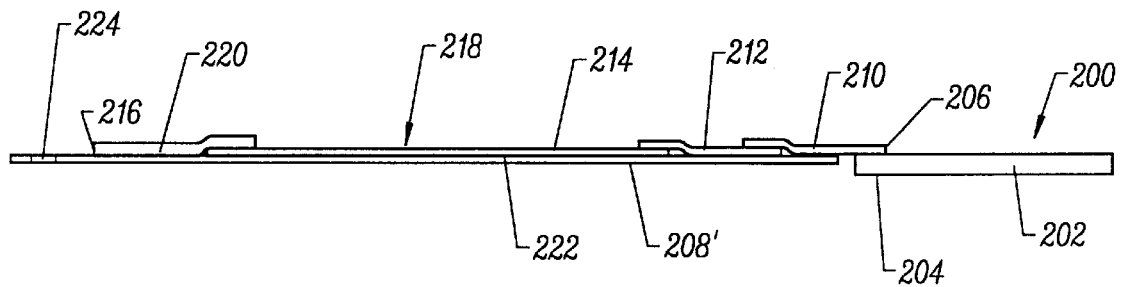
FIG. 10 is a side view of one embodiment of an assay strip suitable for use in an NTX™ assay.
Figure 11:
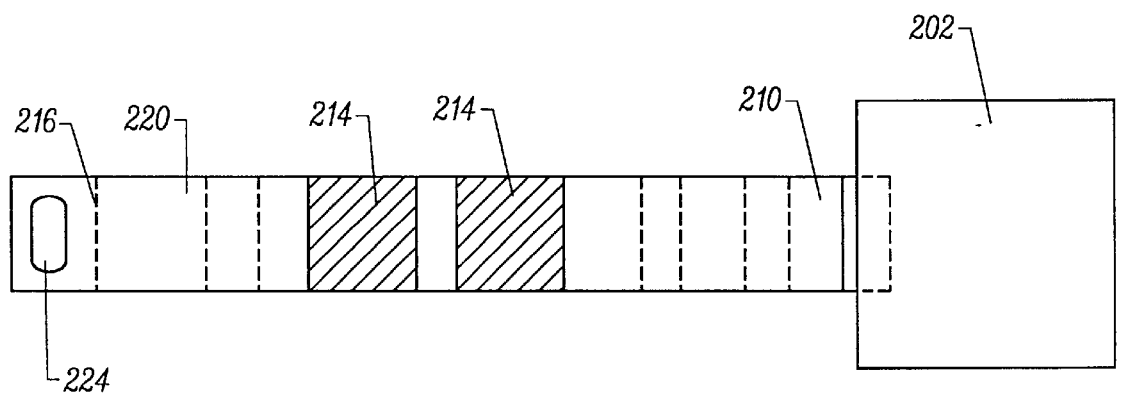
FIG. 11 is a top plan view of the assay strip in FIG. 10.

The sample pads were used as one component of the laminated strip layout 200 illustrated in FIGS. 10 and 11 for an NTX™ assay which is suitable for use in the preferred embodiment of the diagnostic device 60 described above. The strip layout 200 includes a sample distribution pad 202 for receiving the sample through the inlet port (not shown) to the top side 204 of the sample distribution pad 202 at the proximal end 206 of the strip. The distribution pad 202 which is made of material from CytoSep No. 1662 having approximately square dimensions of about 7 mm with a thickness of about 0.023 mm. The sample pad 202 attaches to and is in fluid communication with two assay strips like 114 and 116 previously illustrated in FIG. 9. One of these strips is represented in FIGS. 10 and 11 as assay strip 208 which is made of multiple components.

The sample flows to a sample treatment pad 210 and subsequently to a conjugate pad 212. Both pads 210 and 212 are made of a material from Accuwik No. 14-20 and each is about 4 mm long and 3 mm wide with a thickness of about 0.00945 inches. The conjugate pad 212 contains a diffusively immobilized conjugate of blue polystyrene microparticles with a mouse monoclonal antibody to NTX™ and is in fluid communication with a reagent strip 214 made of nitrocellulose material from Schleicher & Schuell P/N AE98 having a size of about 12.4 mm long and about 3 mm wide with a thickness of about 0.004685 inches. The reagent strip 214 contains the chemical reagents for performing the assay to produce a physically detectable change on the underside 218 of the strip to be measured by the detector previously described. There are two zones of non-diffusively immobilized materials on reagent strip 214: the first zone containing NTX™ antigen and the second zone containing goat antibody to mouse IgG. The reagent strip 214 allows the treated sample to flow quickly towards the distal end 216 of the strip where excess sample is collected by an end pad 220. As seen in FIG. 6, the top face 108 of the optics assembly provides an indentation 84 for each assay strip to accommodate the end pad 220. The end pad is made of material from Schleicher & Schuell P/N GB 002 having dimensions of about 3 mm wide and about 4 mm long with a thickness of about 0.019 inches.

The pads 210, 212, and 214 are supported and attached to a backing material 222 which is made of poly(ethylene terephthalate) plastic from Adhesives Research with an adhesive P/N 8565. The backing material is about 22.5 mm long and about 3 mm wide with a thickness of about 0.01 mm.

Table 2 shows the results for a range of concentrations of NTX™ from about 1 to about 500 nM at four different concentrations of chloride (0, 0.15, 0.25, 0.5). Since the pads were only washed once after dipping, a significant amount of silver remained on the pad which was not bound to the pad matrix. This unbound silver then leached out of the pad during the assay and wicked along with the sample into the test zones. It was observed after the color readings of the test zones were taken that their color became progressively darker as the exposure of the unbound silver now in the test zones to light lengthened.

The Zone 1 response to 1 nM NTX™ reported in Table 2 remained essentially constant (0.72–0.81) up to 0.25M NaCl, and then fell to a reflectance density of 0.5 in the presence of 0.5M NaCl. The pattern for 30 nM NTX™ was very similar. The response of Zone 2 was complementary to that of Zone 1. The assay was thus resistant to NaCl interference up to a concentration of 0.25M.

TABLE 2

| Cl (M) | NTX ™ (nM) | Reflectance Density | |
|---|---|---|---|
| | | Zone 1 | Zone 2 |
| 0 | 1 | 0.81 | 0.16 |
| 0 | 30 | 0.74 | 0.19 |
| 0 | 100 | 0.66 | 0.3 |
| 0 | 500 | 0.33 | 0.45 |
| 0.15 | 1 | 0.72 | 0.28 |
| 0.15 | 30 | 0.74 | 0.26 |
| 0.15 | 100 | 0.81 | 0.3 |
| 0.15 | 500 | 0.36 | 0.44 |
| 0.25 | 1 | 0.76 | 0.32 |
| 0.25 | 30 | 0.67 | 0.28 |
| 0.25 | 100 | 0.54 | 0.32 |
| 0.25 | 500 | 0.32 | 0.42 |
| 0.5 | 1 | 0.5 | 0.41 |
| 0.5 | 30 | 0.5 | 0.44 |
| 0.5 | 100 | 0.33 | 0.35 |
| 0.5 | 500 | 0.37 | 0.46 |

EXAMPLE 4

Additional test assays were performed to evaluate the ability of silver nitrate treated membranes to bind the assay interfering substance chloride using NTX™ assays. In these assays, treated and untreated sample pads measuring 7×7 mm were prepared as described in Example 2. The sample pads were made of CytoSep 1660 or IDA.

Figure 15:
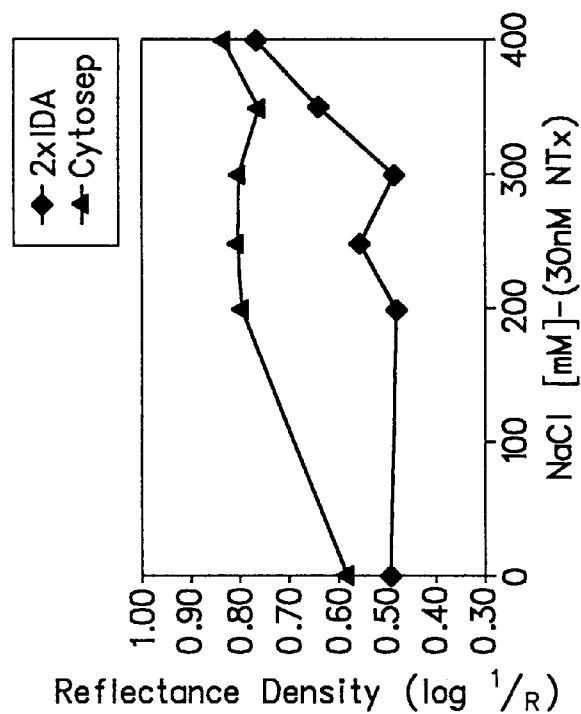
FIG. 15 is a graph of reflectance density (log 1/R) vs. NaCl concentration (mM) in Zone 2 of a 30 nM NTX™ concentration assay for a CytoSep 1660 and a two-layer IDA sample pad membrane.
Figure 14:
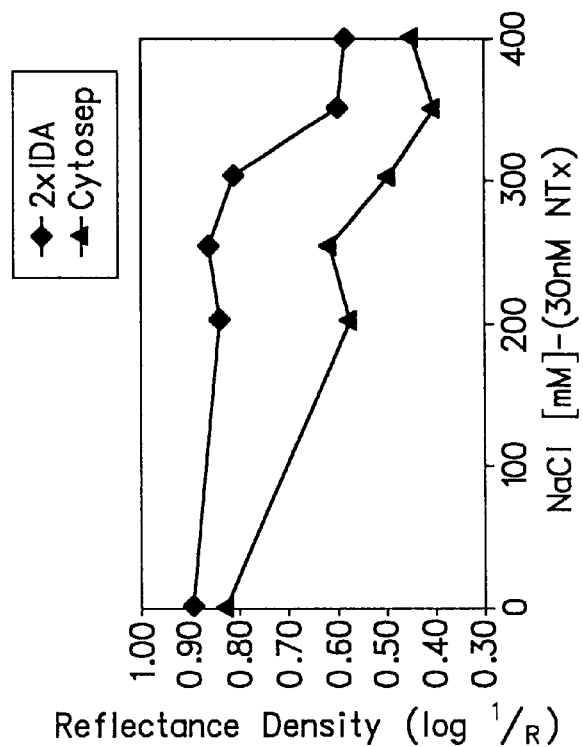
FIG. 14 is a graph of reflectance density (log 1/R) vs. NaCl concentration in Zone 1 of a 30 nM NTX™ concentration assay for a CytoSep 1660 and a two-layer IDA sample pad membrane.

The assay strips were prepared as described in Example 3, except that two layers of IDA material were used. The two layers physically overlapped each other without adhesive therebetween. The reflectance density results for a 30 nM NTX™ sample at various NaCl concentrations ranging from 0 to about 400 mM are presented in FIG. 14 for Zone 1. FIG. 15 presents the reflectance density results for Zone 2 for the strips corresponding to FIG. 14. The silver-IDA material rendered the assay resistant to the effects of NaCl up to a concentration of about 300 mM.

EXAMPLE 5

Additional test assays were performed to evaluate the ability of silver nitrate treated membranes to bind the assay interfering substance chloride using NTX™ assays. In these assays, treated and untreated sample pads measuring 7×7 mm were prepared as described in Example 2. The sample pads were made of CytoSep 1660, C/P30 or IDA.

The assay strips were prepared as described in Example 3, except that for one assay two layers of IDA material were used. The two layers physically overlapped each other without adhesive therebetween.

Figure 16:
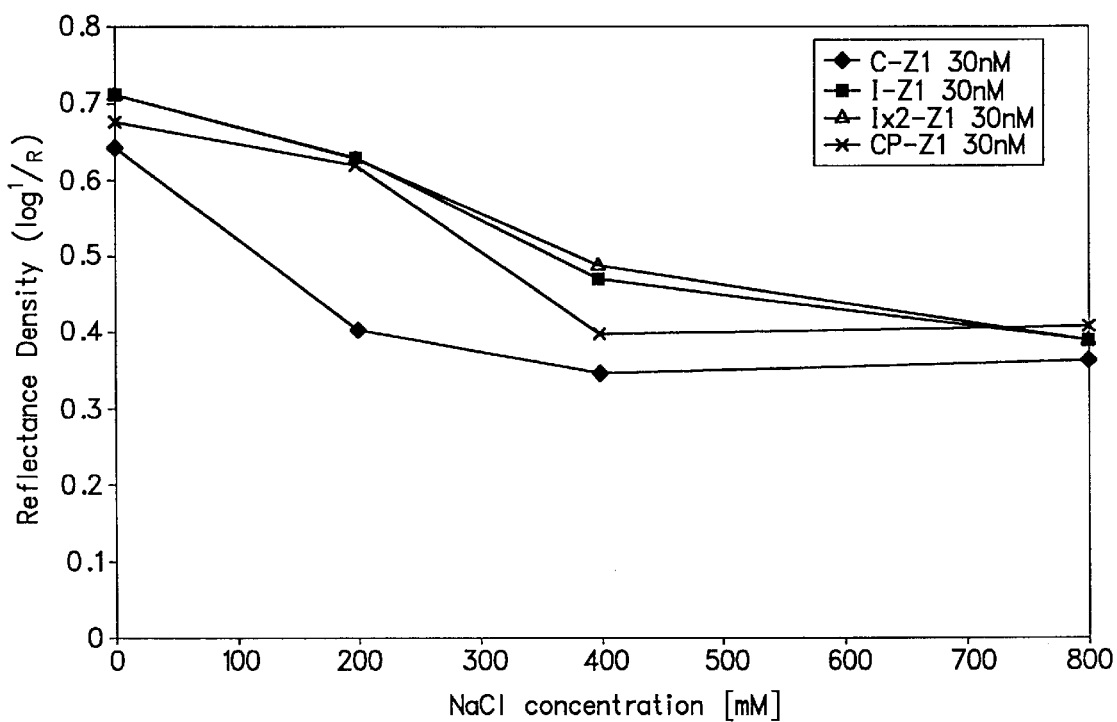
FIG. 16 is a graph of reflectance density (log 1/R) vs. NaCl concentration (mm)in Zone 1 of a 30 nM NTX™ concentration assay for a CytoSep 1660, a one- and a two-layer IDA sample pad membrane, and a C/P30 membrane.

The reflectance density results for a 30 nM NTX™ sample at various NaCl concentrations ranging from 0 to about 800 mM are presented in FIG. 16 for Zone 1.

The greatest resistance to chloride was produced by a sample pad consisting of two layers of silver treated IDA, followed in effectiveness by one layer of silver treated IDA and then one layer of silver treated C/P30. The control sample pad used CytoSep 1660 with no silver treatment which allowed the NaCl to pass through freely and thus would interfere with the NTX™ assay response.

EXAMPLE 6

Another example of a substance which potentially interferes with accurate assay results is ascorbate. To demonstrate the effectiveness of the present invention in solving this problem, several tests were performed using an creatinine assay.

Figure 17:
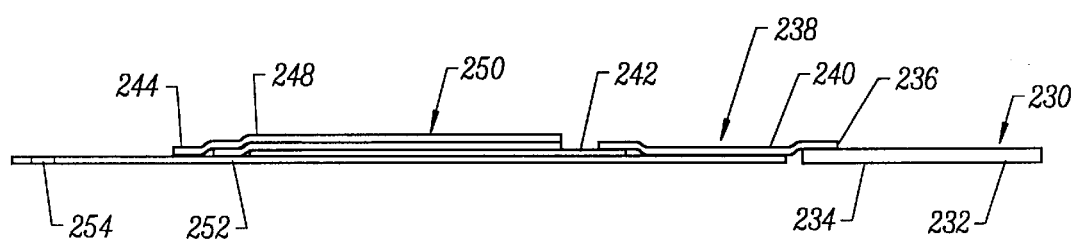
FIG. 17 is a side view of one embodiment of an assay strip suitable for use in a general chemistry assay.
Figure 18:
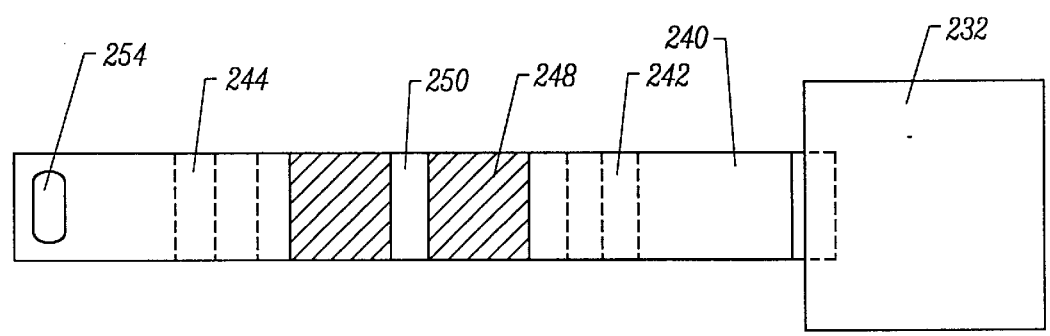
FIG. 18 is a top plan view of the assay strip in FIG. 17.

FIGS. 17 and 18 illustrate a laminated strip layout 230 for a creatinine or other general chemistry assay that is suitable for use in the preferred embodiment of the diagnostic device described above. The strip layout 230 includes a sample pad 232 for receiving the sample through the inlet port (not shown) on the topside 234 of the pad 232 at the proximal end 236 of the strip 238.

The sample pad 232 is made of either CytoSep No. 1660 or GF/QA from Whatman. The GF/QA material from Whatman, Inc. of Fairfield, N.J. which is an quaternary ammonium cellulose matrix having a basis weight of about 68 g/m², a thickness of about 373 μm, and a mean pore size of 4.0 μm. The GF/QA material has a protein binding capacity for bovine serum albumin of 0.296 g/dg with a linear wicking (Klemm) of 2 min for a 7.5 cm rise and a derivative content of 2.0 mg/cm². The GF/QA material includes trimethylhydroxy propyl quaternary ammonium (QA) as a high performance strong base quaternary ammonium exchanger with fast kinetics, high protein capacity, and is effective over a wide pH range.

The material had approximately square dimensions of about 7 mm with a thickness of about 0.023 inches. The sample pad 232 attaches to and is in fluid communication with two assay strips like 114 and 116 previously illustrated in FIG. 9.

The sample flows from the sample pad 232 to a sample treatment pad 240 that is made of a material from Pall Biosupport Accuwik No. 14-20, is about 7 mm long and 3 mm wide with a thickness of about 0.00945 inches. The sample treatment pad 240 is in fluid communication with a transport matrix 242 made of polyester substrate from Tetko P/N 7-2F777 BM having a size of about 11 mm long and about 3 mm wide with a thickness of about 0.00846 inches. The transport matrix 242 allows the treated sample to flow quickly towards the distal end 244 of the strip. Substantially overlapping the transport matrix 242 is a spreading layer 246 that assists in spreading the treated sample across the length of the strip. A reagent layer 248 substantially overlaps the spreading layer 246 and contains the chemical reagents for performing the assay to produce a physically detectable change on the top surface 250 of the reagent layer that is measured by the detector previously described. The reagent layer contains the dried chemical components needed to measure creatinine in the sample: the solution for dipping the indicator included 0.5% w/v sucrose, 1.0% w/v polyvinyl-pyrrolidone (avg. mw. about 40,000), 5% v/v surfactant 10G (p-isononylphenoxypoly(glycidol)) and 75 mg/ml bis(4-(N-(3'-sulfo-n-propyl)-N-n-propyl)amino-2,6-dimethylphenyl)methane, disodium salt; the enzyme solution used for dipping the reagent layer included 1000 u/ml horse radish peroxidase (EC 1.11.17), 500 u/ml sarcosive oxidase (EC 1.5.3.1), 5000 u/ml creatinine amidinohydrolase (EC 3.5.3.3), 1200 u/ml creatinine amidohydrolase (EC 3.5.2.10) (all from the Toyobo Company), 1% w/v poly (vinyl alcohol) (avg. mw. about 70,000), 1% v/v Triton X-100 (t-octylphenoxypolyethoxyethanol), 1% w/v sucrose, 5 mg/ml Bovine Serum Albumin, and 50 mM buffer 3-(N-morpholino)-2-hydroxypropanesulfonic acid, sodium salt, pH 7.5.

The sample treatment pad 240 and the transport matrix 242 are supported and attached to a backing material 252 which is made of poly(ethylene terephthalate) plastic from Adhesives Research with an adhesive P/N 8565. The backing material is about 22.5 mm long and about 3 mm wide with a thickness of about 0.01 mm.

In Table 3, each of the assay strips 230 contained about 30 mM of Creatinine and used a spreading membrane 246 made of Biodyne C. A control strip having no ascorbic acid is compared to strips exposed to 300 mg/dL of ascorbate in a 45 µL sample. As seen in Table 3, the color contrast is reduced with the presence of ascorbic acid on the CytoSep 1660 sample pad compared to the control with no ascorbic acid. The deleterious affect of the ascorbic acid is reversed by using the Whatman GF/QA material as the sample pad. The color contrast is fully restored as indicated by the increase in the average K/S values. The sample pad made of GF/QA material was able to remove at least 300 mg/dL of ascorbate from a 45 µL sample. To ensure that the change in color contrast was not being caused by the ascorbate simply changing the pH, a buffer agent like 3-(N-Morpholino)-2-hydroxypropanesulfonic acid (MOPSO) was added in various amounts to the sample pads. The absence or addition of the various amounts of MOPSO did not affect the color contrast, indicating that the changes in color contrast were caused by the ascorbate deleteriously affecting the assay results. The assay results in Table 3 are presented in units of K/S calculated using the equation $K/S=(1-R)^2/2R$; wherein R is reflectance; from Kubelka and Munk, Z. Techn. Phys., 12, 593–601 (1933) and explained in Werner and Rittersdorf, Methods of Enzymatic Analysis, Vol. I, pp. 305–326 (Verlag Chemie, 1983).

TABLE 3

| Ascorbic Acid mg/dL | Creatinine mM | Sample Pad | Sample Pad MOPSO mM | Avg K/S |
|---|---|---|---|---|
| 0 | 30 | CS 1660 | 50 | 3.2 |
| 300 | 30 | CS 1660 | 50 | 1.8 |
| 300 | 30 | CS 1660 | 100 | 1.9 |
| 300 | 30 | CS 1660 | 500 | 1.8 |
| 300 | 30 | GF/QA | 50 | 4.0 |
| 300 | 30 | GF/QA | 0 | 4.4 |

EXAMPLE 7

Figure 19:
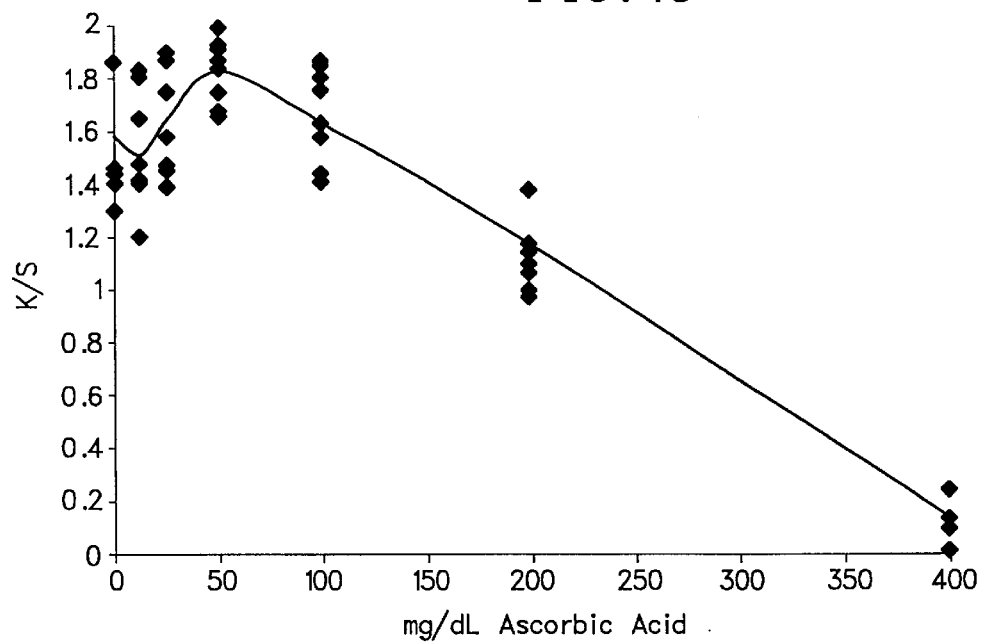
FIG. 19 is a graph of the K/S value vs. the ascorbic acid concentration (mg/dL) for a GF/QA sample pad for a 15 mM Creatinine sample.

Another example of the effectiveness of the present invention at removing an interfering substance such as ascorbate from a sample to improve the accuracy of assay results is demonstrated in FIG. 19. Several assay strips were prepared in the manner described in the previous example and used to perform an assay on samples each containing about 15 mM of Creatinine. The sample pads for each assay were made of the Whatman GF/QA material. Even with samples having a Creatinine concentration that was significantly lower then the previous example, FIG. 19 shows that the color contrast remained relatively unaffected by the ascorbic acid until the level exceeded about 200 mg/dL.

Numerous modifications and variations of the present invention are possible in light of the above teachings. It is therefore to be understood that within the scope of the appended claims, the invention may be practiced otherwise than as specifically described herein.

What is claimed is:

1. A transport matrix for removing one or more substances which interfere with determining the presence of an analyte in an immunoassay sample of physiological fluid, the transport matrix adapted for use in a sealed housing of an immunoassay device, the transport matrix comprising:

a sample receptor zone configured to receive the sample of physiological fluid directly on the matrix;

a detection zone having an immunoassay reagent yielding a physically detectable change which correlates with the amount of selected analyte in the sample to provide a quantitative immunoassay result within the housing, the detection zone being in fluid communication by capillary action with the sample receptor zone; and an active chemical component including silver or lead is immobilized by chemically binding on the transport matrix prior to the detection zone, the active chemical component having an affinity for binding to and immobilizing the interfering substance, the active chemical component being insoluble in the sample of physiological fluid.

2. The transport matrix of claim 1 wherein the transport matrix further comprises a solid phase support being immobilized within the transport matrix whereby the active chemical component is immobilized on the solid phase support which is also immobilized within the transport matrix.

3. The transport matrix of claim 2 wherein the solid phase support is a nonporous material and the transport matrix is a porous material.

4. The transport matrix of claim 3 wherein the non-porous solid phase support is selected from a group consisting of beads, magnetic particles, paramagnetic particles, microparticles, and macroparticles.

5. The transport matrix of claim 1 wherein the active chemical component is immobilized directly on the transport matrix.

6. The transport matrix of claim 1 wherein the transport matrix is selected from the group consisting of carboxymethyl polymers, diethylaminoethyl polymers, sulfoxyethyl polymers, trimethylhydroxy propyl quaternary ammonium polymers, orthophosphate polymers, iminodicarboxylic acid polymers, diethylaminoethyl Sephadex polymers, diethyl amino ethyl Sephadex polymers, Sepharose polymers, epichlorohydrin triethanolamine cellulose polymers, polyethyleneimine cellulose polymers, quaternary alkylamine polymers, quaternary alkylalkanolamine polymers, trimethylbenzylammonium polymers, dimethylethanolbenzylammonium polymers, trimethylbenzylammonium polymers, dimethylethanolamine polymers, polyamine polymers, alkylamine polymers, quaternary ammonium polymers, tertiary amine polymers, carboxymethyl Sephadex polymers, sulfopropyl Sephadex polymers, sulfoxyethyl cellulose polymers, sulfonic acid polymers, nuclear sulfonic acid polymers, carboxylic acid polymers, and triethylaminoethyl cellulose polymers.

7. The transport matrix of claim 6 wherein the transport matrix has a derivative content in an amount less than about 10 mg/cm$^2$ which effectively immobilizes the interfering substance.

8. The transport matrix of claim 1 wherein the active chemical component is applied to the transport matrix in an amount less than about 1M which effectively immobilizes the interfering substance.

9. The transport matrix of claim 1 wherein the amount of active chemical component immobilized on the transport matrix provides about the same number of binding sites as the amount of interfering substance in the assay sample.

10. An immunoassay device for removing one or more substances which interfere with determining the presence of an analyte in an immunoassay sample of physiological fluid, the device comprising:

a housing having an exterior surface and sealing an interior space;

sample receptor means for directly receiving the sample of physiological fluid containing an analyte selected for determining its presence, the sample receptor means being located on the exterior surface of the housing; and a transport matrix located within the interior space of the housing and in fluid communication with the sample receptor means, the transport matrix having:

a sample receptor zone configured to directly receive the sample of physiological fluid from the sample receptor means;

a detection zone having a immunoassay reagent yielding a physically detectable change which correlates with the amount of selected analyte in the sample to provide a quantitative immunoassay result within the housing, the detection zone being in fluid communication by capillary action with the sample receptor zone; and an active chemical component including silver or lead is immobilized by chemically binding on the transport matrix prior to the detection zone, the active chemical component having an affinity for binding to and immobilizing the interfering substance, the active chemical component being insoluble in the sample of physiological fluid.

11. The immunoassay device of claim 10 wherein the active chemical component is immobilized directly on the transport matrix.

12. The immunoassay device of claim 10 wherein the transport matrix is selected from the group consisting of carboxymethyl polymers, diethylaminoethyl polymers, sulfoxyethyl polymers, trimethylhydroxy propyl quaternary ammonium polymers, orthophosphate polymers, iminodicarboxylic acid polymers, diethylaminoethyl Sephadex polymers, diethyl aminoethyl Sephadex polymers, Sepharose polymers, epichlorohydrin triethanolamine cellulose polymers, polyethyleneimine cellulose polymers, quaternary alkylamine polymers, quaternary alkylalkanolamine polymers, trimethylbenzylammonium polymers, dimethylethanolbenzylammonium polymers, trimethylbenzylammonium polymers, dimethylethanolamine polymers, polyamine polymers, alkylamine polymers, quaternary ammonium polymers, tertiary amine polymers, carboxymethyl Sephadex polymers, sulfopropyl Sephadex polymers, sulfoxyethyl cellulose polymers, sulfonic acid polymers, nuclear sulfonic acid polymers, carboxylic acid polymers, and triethylaminoethyl cellulose polymers.

13. The immunoassay device of claim 12 wherein the transport matrix has a derivative content in the amount of about 2.5 mg/cm$^2$ to about 2.0 mg/cm$^2$.

14. The immunoassay device of claim 10 wherein the active chemical component is applied to the transport matrix in an amount less than about 1M which effectively immobilizes the interfering substance.

15. The immunoassay device of claim 10 wherein the amount of active chemical component immobilized on the solid phase support provides about the same number of binding sites as the amount of interfering substance in the assay sample.

\* \* \* \* \*